United States Patent [19]
Pitt et al.

[11] Patent Number: 4,917,793
[45] Date of Patent: Apr. 17, 1990

[54] TRANSPARENT POROUS MEMBRANE HAVING HYDROPHILIC SURFACE AND PROCESS

[76] Inventors: Aldo M. Pitt, 18 Partridge La., Sudbury, Mass. 01776; Michael J. Steuck, 89 Central St., N. Reading, Mass. 01864

[21] Appl. No.: 937,755

[22] Filed: Dec. 4, 1986

[51] Int. Cl.$^4$ ............................................. B01D 13/00
[52] U.S. Cl. ........................................ 210/94; 210/490; 210/500.35; 210/500.38; 210/500.36; 428/315.7; 428/315.9; 435/284
[58] Field of Search ................... 210/490, 94, 500.36, 210/500.35, 500.38, 321.64; 428/422, 315.5, 315.7, 315.9; 435/284, 180; 436/531, 807

[56] References Cited

U.S. PATENT DOCUMENTS

| | | | |
|---|---|---|---|
| 4,220,153 | 9/1980 | Dresback | 604/892 |
| 4,230,463 | 10/1980 | Henis et al. | 55/16 |
| 4,298,002 | 11/1981 | Ronel et al. | 604/891 |
| 4,387,024 | 6/1983 | Kurihara et al. | 210/500.41 |
| 4,546,083 | 10/1985 | Meyers et al. | 435/284 |
| 4,618,533 | 10/1986 | Steuck | 428/315.7 |
| 4,627,850 | 12/1986 | Deters et al. | 210/500.28 |
| 4,645,602 | 2/1987 | Barnes, Jr. et al. | 210/490 |
| 4,670,146 | 5/1987 | Inoue et al. | 210/500.36 |
| 4,705,636 | 11/1987 | Small et al. | 210/500.42 |

FOREIGN PATENT DOCUMENTS 0148161  7/1985  European Pat. Off. ............ 435/284

*Primary Examiner*—W. Gary Jones
*Assistant Examiner*—Coreen Y. Lee
*Attorney, Agent, or Firm*—Andrew T. Karnakis; Paul J. Cook

[57] ABSTRACT

A composite, microscopically transparent, porous membrane is formed from a porous polytetrafluoroethylene membrane having desired bulk properties on which is directly coated a cross-linked polymer having desired surface properties. The composite membrane retains the porosity of the porous polymeric membrane.

14 Claims, 1 Drawing Sheet

TRANSPARENT POROUS MEMBRANE HAVING HYDROPHILIC SURFACE AND PROCESS

BACKGROUND OF THE INVENTION

This invention relates to a porous, microscopically transparent membrane having bulk properties which differ from its surface properties and to a process for making the same. More particularly, this invention relates to a transparent microporous or ultrafiltration membrane formed from a polytetrafluoroethylene substrate wherein the substrate is hydrophobic and opaque or translucent in its unmodified form and is rendered hydrophilic and transparent when wet with aqueous media and to a process for forming such a membrane. This invention also relates to a device utilizing the membrane of this invention for observing cell growth.

As used herein, the term "transparent" means microscopically transparent. That is, the membrane is transparent to the extent that normal sized cells, e.g., 5 to 30 microns, can be viewed through the membrane wall with a microscope such as at 50 times to 600 times magnification. The transparency can be specifically quantified by measuring optical density with visible light such as with a spectrophotometer. The optical density of the wet membrane of this invention is between 0 and 0.5, preferably 0 to 0.3 when measured with a spectrophotometer at 410 nanometers visible light.

In many applications of membrane technology, it is desirable to utilize a membrane filter which is mechanically strong, is thermally stable, is relatively inert chemically and is insoluble in most organic solvents. Often, it is desirable that the membrane have surface properties which are radically different from and sometimes incompatible with the bulk properties set forth above. In some instances it is desired to form a porous membrane which is transparent and which is capable of supporting cell growth in order that cell growth can be easily monitored merely by microscopic examination of the live cells through the membrane. For example, in cell growth technology it is desirable to effect cell growth on and within the pores of a membrane rather than on a flat surface so that three dimensional cell growth rather than two dimensional cell growth can be effected. This is particularly true when growing epithelial cells such as those derived from the lungs, kidneys, or intestine which demonstrate a distinct polarity. Prior to the present invention, porous membranes used for cell growth are opaque or translucent so that the progress of cell growth cannot be viewed. At the present time, it is necessary to take a subsample of the cells under conditions toxic to the cells in order to ascertain the level of cell growth. This is undesirable since it reduces the number of cells available for producing the desired cell product or cell marker. Therefore, it would be desirable to provide a transparent membrane capable of permitting cell growth under conditions that the extent of cell growth can be observed visually.

It is known that polytetrafluoroethylene can be rendered transparent in water by immersing it in 100% methanol followed by immersing it sequentially into methanol-water mixtures and lastly in 100% water. However, the polytetrafluoroethylene surface is not rendered hydrophilic by such a wetting procedure. In addition, this procedure is inconvenient for the end user and the membrane cannot be rewet if allowed to dry.

Conventional methodology presently used to achieve the duality of function of bulk properties which differ from the surface properties is to coat a preformed membrane having the desired bulk properties with an oligomer or polymer having the desired surface properties. Typical coating materials include surfactants, many of which are toxic to cells, and water soluble polymers such as polyvinylpyrrolidone. This approach to modifying surface properties is undesirable since the coating is only temporary and exposure to any process fluid, particularly when the substrate having the desired bulk properties is a porous membrane, effects removal of the coating from the porous membrane. Membranes treated in this fashion cannot be steam sterilized, cannot be rewet once dried after being wetted with water and exhibit high extractable levels. These properties are unacceptable in many filtration applications, particularly when processing biological fluids which are to be sterilized or subsequently analyzed. This is particularly true in cell culture since many of these extractables are cytotoxic and, therefore, incompatible with cell growth.

It also has been proposed to utilize graft polymerization techniques to modify the surface characteristics of a polymeric substrate. Typical examples of graft polymerization are shown for example in U.S. Pat. Nos. 3,253,057; 4,151,225; 4,278,777 and 4,311,573. It is difficult to utilize presently available graft polymerization techniques to modify the surface properties of the porous membrane. This is because it is difficult to modify the entire surface of the membrane including the surfaces within the pores while avoiding pore blockage and while retaining membrane porosity In U.S. Pat. No. 4,340,482, issued July 20, 1982, it has been proposed to modify the surface of porous membranes formed from hydrophobic fluorine-containing polymers by binding a primary amine such as glycine to the hydrophobic substrate. The primary amine renders the polymer surface hydrophilic and can be utilized as a reactant site to link a polymerizable monomer to the porous membrane thereby to obtain a porous membrane having surface properties corresponding to that of the polymerized monomer. Unfortunately, the modified membranes so-produced exhibit properties which are undesirable for use with certain materials. Thus, the membrane so-produced oftentimes is colored, that is, a nonwhite color, and gives off colored, extractable compositions during use. Furthermore, the membranes have a tendency to adsorb proteins from solution and therefore are unacceptable in some applications such as in clinical diagnostic assays and immunofluorescent procedures. U.S. Pat. 4,618,533 discloses a process for modifying the surface characteristics of a porous membrane without plugging the pores of the membrane. There is no disclosure of modifying the bulk properties of the substrate membrane.

Accordingly, it would be highly desirable, for example, to provide a composite membrane having both desirable bulk physical strength and chemical resistance while having desired surface properties different from the bulk properties. Furthermore, it would be desirable to provide a membrane which is not absorptive to light and is microscopically transparent by virtue of surface modification thereof, which is characterized by very low levels of extractables and which exhibits very low adsorptivity for proteins. In addition, it would be desirable to provide a means for rendering a normally translucent or opaque membrane transparent without interfering with cell growth and viability.

SUMMARY OF THE INVENTION

This invention provides a hydrophilic composite porous membrane which is transparent in an aqueous liquid comprising a porous polytetrafluoroethylene membrane substrate and having a permanent coating grafted and/or deposited thereon for the entire porous membrane including the inner pore walls which coating does not interfere with the transparency and which has physical and chemical properties different from the bulk properties of the porous membrane. Unlike the composite membrane products of the prior art, the coating polymer is directly coated onto the substrate polymer without the utilization of an intermediate binding chemical moiety. The bulk properties of the polytetrafluoroethylene porous membrane include inertness to most organic solvents, inertness to many chemical reagents, adequate tensile strength and ductility. The surface of the composite membrane is hydrophilic, has a very low level of extractables and does not have colored extractables. Since the membrane is transparent and nontoxic, it is useful as an environment for cell culture and for monitoring cell growth by direct microscopic examination.

BRIEF DESCRIPTION OF THE DRAWING

The figure is an cross-sectional view of the device of this invention which incorporates the membrane of this invention.

DESCRIPTION OF SPECIFIC EMBODIMENTS

Figure 1:
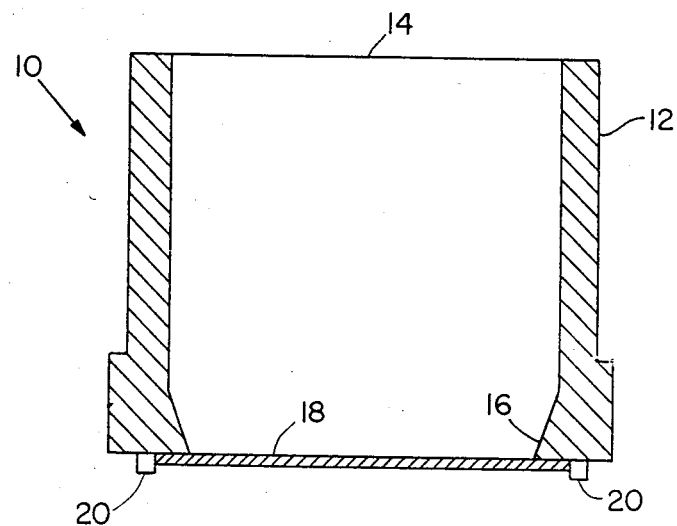

In accordance with this invention a polytetrafluoroethylene porous membrane is directly coated throughout its entire surface with a hydrophilic, polymerized, cross-linked monomer having the desired surface properties. The monomer is deposited on the surfaces of the porous membrane by graft polymerization and/or by deposition of the cross-linked monomer. The desired deposition of the cross-linked monomer onto the porous membrane is effected as a direct coating and does not require or utilize an intermediate binding chemical moiety such as an amino acid or the like. The coating is between about 10 and 200 Angstroms thick, preferably between about 20 and 100 Angstroms thick. At thicknesses below about 10 Angstroms the membrane is not sufficiently hydrophilic. At thicknesses above about 200 Angstroms, the optical properties of the membrane are impaired. Generally, the porous polytetrafluoroethylene membrane has an average pore size between about 0.001 and 10 microns and more usually between about 0.1 and 5.0 microns.

The polymerization and cross-linking of the polymerizable monomer to the porous polytetrafluoroethylene membrane by grafting and/or deposition must be effected so that the entire surface of the porous membrane including the inner surfaces of the pores is coated entirely with a cross-linked/grafted polymer. In one process embodiment, the porous membrane is washed in a first step with a solvent that does not swell or dissolve the porous membrane and which wets the surfaces of the pores. Suitable solvents for this purpose include methanol, ethanol, 2-propanol, acetone, tetrahydrofuran or the like. The purpose of this wetting step is to assure that the monomer composition subsequently contacted with the porous membrane wets the entire surface of the porous membrane. The membrane then is washed in water. This preliminary wetting step can be eliminated in a second process embodiment when the solvent composition described below itself functions to wet the entire surface of the porous membrane. This can be effected when the reagent bath contains a high concentration of organic solvent, between about 80 and 95% by weight. In either the first or second process embodiment all that is required is that the entire porous surface be wet so that the polymerizable monomer wets the entire surface of the porous membrane.

Subsequent to wetting the porous membrane, a reagent bath comprising a free radical polymerizable monomer, a polymerization initiator and cross-linking agent in a solvent comprising water and a water miscible, polar, organic solvent for these three constituents is contacted with the porous membrane under conditions to effect free radical polymerization of the monomer and coating of the porous membrane with the cross-linked polymer. When the monomer is difunctional or has higher functionality, an additional cross-linking agent need not be utilized. In the first process embodiment when the organic solvent comprises between about 10 and 75 weight, preferably between about 20 and 60 weight percent, based upon the weight of the solution, the coated polytetrafluoroethylene membrane is rendered transparent by virtue of the surface coating treatment. This effect is not observed when the solvent is entirely water or entirely organic solvent.

Any monomer for coating the polymer can be utilized herein so long as it is capable of being polymerized by free radical polymerization and can be cross-linked. Representative suitable polymerizable monomers include hydroxyalkyl acrylates or methacrylates including 1-hydroxyprop-2-yl acrylate and 2-hydroxyprop-1-yl acrylate, hydroxypropyl methacrylate, 2,3-dihydroxypropyl acrylate, hydroxyethyl acrylate, hydroxyethyl methacrylate or the like or mixtures thereof. Other polymerizable monomers which can be utilized herein include acrylic acid, 2-N,N-dimethylaminoethyl methacrylate, sulfoethyl methacrylate or the like, acrylamides, methacrylamides, ethacrylamides, etc. These monomers are examples of polar-substituted or functionally substituted monomers useful herein.

Suitable initiators and cross-linking agents for the monomers set forth above are well known in the art. For example, when utilizing acrylates as the polymerizable monomer, suitable polymerization initiators include ammonium persulfate, potassium persulfate, 4,4'-azobis(4-cyanovaleric acid), 2,2'-azobis(2-amidinopropane) hydrochloride, potassium hydrogen persulfate or the like. When utilizing acrylates or methacrylates or methacrylamides as the polymerizable monomer, suitable cross-linking agents include difunctional acrylates, methacrylates or acrylamides such as tetraethylene glycol diacrylate, glycidyl acrylate or methylene bisacrylamide or the like. In one embodiment of this invention, cross-linking agents having difunctionality or higher functionality can be utilized without an additional monomer in the coating of this invention. The monomer, polymerization initiator and cross-linking agents are contacted with the porous membrane as a mixture in a solvent which is compatible with the three reactants and the porous membrane so that the desired free radical polymerization and cross-linking is achieved without the formation of a significant amount of slowly extractable by-products and without the formation of colored products. If readily extractable by products are formed, these can be removed by conducting a washing step in a suitable solvent subsequent to the coating step.

The particular solvent composition employed for the polymerizable monomer, polymerization initiator and cross-linking agent will depend upon the particular reactants employed. All that is necessary is that the reactants dissolve in the solvent and are capable of being reacted by free radical initiation in the solvent system and that the solvent does not attack the porous polytetrafluoroethylene membrane substrate. In general, water-miscible, polar, aprotic solvents are most effective in producing transparent, hydrophilic polytetrafluoroethylene membranes. Representative suitable solvent compositions include (a) water and (b) a water-miscible organic solvent such as N-methylpyrrolidone, dimethyl sulfoxide, 2-propanol, tetrahydrofuran, propylene carbonate, gammabutyrolactone, tetrahydrothiophene-1,1-dioxide, N-cyclohexyl-2-pyrrolidone, tetramethylurea or the like.

Generally, the polymerizable monomer is present in the reactant solution at a concentration between about 1% and about 20%, preferably between about 3% and about 9% based upon the weight of the reactant solution. The cross-linking agent generally is present in an amount of between about 0.4% and about 100% by weight, preferably between about 10% and about 50% by weight based upon the weight of the polymerizable monomer. Greater amounts of cross-linking agents can be used but no significant advantage is gained thereby. The polymerization initiator is present in an amount of between about 1% and about 60% by weight, preferably between about 10% and about 35% by weight, based upon the weight of the polymerizable monomer. The concentration of initiator utilized herein is much higher than normally utilized when polymerizing monomers. Polymerization initiators are normally used at a concentration of about 0.1 wt. % based upon the weight of monomer. It is believed that the high concentration of initiator used herein limits the length of the polymer chains thereby avoiding pore plugging while uniformly coating the entire exposed pore surface of the substrate polymer. As noted above, the cross-linking agent can be utilized without the monomer nd thereby functions as the polymerizable monomer.

Any conventional energy source for initiating free radical polymerization can be employed such as heating, ultraviolet light, gamma radiation, electron beam radiation or the like. For example, when free radical polymerization is initiated by heating, the reactant solution and the porous membrane are heated to a temperature at least about 60° C. and up to the temperature at which undesirable bulk polymerization occurs in solution or at which the solvent begins to boil. For example, generally suitable temperatures when utilizing an aqueous solvent system between about 80° C. and about 95° C., preferably between about 88° C. and about 92° C. The polymerization reaction should be effected for a time to assure that the entire exposed surface of the porous membrane is coated with the deposited polymer composition but without plugging of the pores in the membrane. Generally, suitable reaction times are between about 0.1 and about 30 minutes, preferably between about 1 and about 4 minutes. Reaction can be effected while the porous membrane is immersed in solution. However, this will result in the polymerization of the monomer throughout the solution. It is preferred to saturate the porous membrane with the reactant solution and to effect reaction outside of the solution so that monomer is not wasted. Thus, the reaction can be conducted batchwise or continuously. When operating as a continuous process, a sheet of porous membrane is saturated with the reactant solution and then transferred to a reaction zone where it is exposed to energy to effect the polymerization reaction. For use in attachment dependent cell growth, the hydrophilic membrane is coated with a composition which promotes cell adherence such as fibronectin, collagen, laminin or mixtures thereof. The membrane immersed in an aqueous mixture of the composition and then dried. For use with suspension cultures of cells, the membrane is used without additional treatment. Referring to the FIG. 1, the device of this invention 10 includes a hollow tubular member 12 having one open end 14 and a closed end 16. The closed end 16 comprises the treated membrane 18 of this invention which is sealed, such as by heat sealing or with an adhesive to the entire periphery of end 16. It is preferred that tubular member 12 be transparent in order to enhance viewing of cell growth within membrane 18. In use, viable cells are introduced into membrane 18 and the closed end 16 is immersed into an aqueous growth medium. Prior to introducing the cells into the membrane, the membrane pores are coated with a composition which promotes cell adhesion as set forth above. It is to be understood that the tubular member can have a cross sectional shape such as rectangular, square, circular, elliptical or the like so long as cell growth is not inhibited. Protrusions 20 are provided to space the membrane 18 apart from a surface upon which the device 10 is positioned during use.

EXAMPLES 1–16

In this example, microporous polytetrafluoroethylene with an average pore diameter of 0.45 micrometer was treated. Sixteen aqueous solutions, each containing 25 weight percent N-methylpyrrolidone, were prepared with the compositions listed in Table 1.

TABLE 1

| Example No. | % HPA* | % TEGDA* | % AmPS* |
|---|---|---|---|
| 1 | 3 | 0.5 | 1 |
| 2 | 3 | 1.0 | 1 |
| 3 | 3 | 1.5 | 1 |
| 4 | 3 | 2.0 | 1 |
| 5 | 4 | 0.5 | 1 |
| 6 | 4 | 1.0 | 1 |
| 7 | 4 | 1.5 | 1 |
| 8 | 4 | 2.0 | 1 |
| 9 | 5 | 0.5 | 1 |
| 10 | 5 | 1.0 | 1 |
| 11 | 5 | 1.5 | 1 |
| 12 | 5 | 2.0 | 1 |
| 13 | 6 | 0.5 | 1 |
| 14 | 6 | 1.0 | 1 |
| 15 | 6 | 1.5 | 1 |
| 16 | 6 | 2.0 | 1 |

*HPA = mixture of 2-hydroxyprop-1-yl acrylate (75%) and 1-hydroxyprop-2-yl acrylate (25%)
*TEGDA = tetraethylene glycol diacrylate
*AmPS = ammonium persulfate Sheets of microporous poly(tetrafluoroethylene), 8"×", were wet in 2-propanol and exchanged into 25 weight percent aqueous N-methylpyrrolidone. The sheets were then soaked in the treatment solutions described in Table 1. The sheets were then sandwiched between sheets of polyester and heated at 95° for two minutes. The sheets were rinsed in water and then dried. The sheets were characterized by water rewettability and by light absorbance at 410 nanometers. The results are shown in Table 2.

TABLE 2

| Example No. | Water Rewettable | Optical Density (410 nm) |
| --- | --- | --- |
| 1 | No | 2.0 |
| 2 | No | 2.0 |
| 3 | Yes | 0.33 |
| 4 | Yes | 0.44 |
| 5 | No | 2.0 |
| 6 | No | 2.0 |
| 7 | Yes | 0.36 |
| 8 | Yes | 0.42 |
| 9 | No | 2.0 |
| 10 | Yes | 0.62 |
| 11 | Yes | 0.38 |
| 12 | Yes | 0.40 |
| 13 | No | 2.0 |
| 14 | Yes | 0.42 |
| 15 | Yes | 0.38 |
| 16 | Yes | 0.48 |
| Control* | No | 0.13* |

*Control is untreated poly(tetrafluoroethylene). To read optical density, control was wet first in ethanol and exchanged into 50 weight percent aqueous ethanol.

EXAMPLE 17-32

These examples used microporous poly(tetrafluoroethylene) with an average pore diameter 0.2 micrometer.

Sixteen aqueous solutions, each containing 25 weight percent N-methylpyrrolidone, were prepared with the compositions listed in Table 3.

TABLE 3

| Example No. | % HPA* | % TEGDA* | % AmPS* |
| --- | --- | --- | --- |
| 17 | 3 | 0.5 | 1 |
| 18 | 3 | 1.0 | 1 |
| 19 | 3 | 1.5 | 1 |
| 20 | 3 | 2.0 | 1 |
| 21 | 4 | 0.5 | 1 |
| 22 | 4 | 1.0 | 1 |
| 23 | 4 | 1.5 | 1 |
| 24 | 4 | 2.0 | 1 |
| 25 | 5 | 0.5 | 1 |
| 26 | 5 | 1.0 | 1 |
| 27 | 5 | 1.5 | 1 |
| 28 | 5 | 2.0 | 1 |
| 29 | 6 | 0.5 | 1 |
| 30 | 6 | 1.0 | 1 |
| 31 | 6 | 1.5 | 1 |
| 32 | 6 | 2.0 | 1 |

*HPA = mixture of 2-hydroxyprop-1-yl acrylate (75%) and 1-hydroxyprop-2-yl acrylate (25%)
*TEGDA = tetraethylene glycol diacrylate
*AmPS = ammonium persulfate The treatment procedure described in Examples 1-16 was followed. The results are shown in Table 4.

TABLE 4

| Example No. | Water Rewettable | Optical Density (410 nm) |
| --- | --- | --- |
| 17 | No | — |
| 18 | No | — |
| 19 | Yes | 0.33 |
| 20 | Yes | 0.25 |
| 21 | No | — |
| 22 | No | — |
| 23 | Yes | 0.26 |
| 24 | Yes | 0.26 |
| 25 | No | — |
| 26 | No | — |
| 27 | Yes | 0.31 |
| 28 | Yes | 0.33 |
| 29 | No | — |
| 30 | No | — |
| 31 | Yes | 0.30 |
| 32 | Yes | 0.40 |
| Control* | No | 0.13* |

*Control is untreated poly(tetrafluoroethylene). To read optical density, control was wet first in ethanol and exchanged into 50 weight percent aqueous ethanol.

EXAMPLES 33-37

Continuous rolls of microporous poly(tetrafluoroethylene) membranes with pore diameters of 0.22, 0.45, and 1.0 micrometer were treated in substantially the same fashion as Examples 1-16 using an aqueous solution of 5% HPA, 1.5% TEGDA, 1% AmPS, and 25% N-methylpyrrolidone. All the treated membranes wet instantly in water. The thickness of the untreated membranes and the optical density of the treated membranes are shown in Table 5.

TABLE 5

| Example No. | Pore Size (Micrometer) | Thickness (Micrometer) | Optical Density (410 nm) |
| --- | --- | --- | --- |
| 33 | 0.2 | 23 | 0.064 |
| 34 | 0.2 | 61 | 0.159 |
| 35 | 0.2 | 85 | 0.317 |
| 36 | 0.45 | 105 | 0.257 |
| 37 | 1.0 | — | 0.200 |

EXAMPLE 38

The membrane was incorporated by sealing into a hollow tubular cell culture device which then was sterilized by standard ethylene oxide gas procedures. Vitrogen TM bovine skin type 1 collagen (Collagen Corp., Palo Alto, CA) was diluted in sterilized 0.01 N HCl (1 part collagen: 9 parts acid) and 100 ul was added to each cell culture device and allowed to dry in a laminar flow hood. Madin Darby Canine Kidney (MDCK ATCC No. 34) cells were cultured in Dulbecco's Modified Eagle's Medium (DMEM) containing 10% fetal bovine serum (FBS), 1% L-glutamine, 1% nonessential amino acids, 100 ug/ml penicillin, 100 ug/ml streptomycin; and 10 uM HEPES. The cells were inoculated into the collagen coated cell culture device of this invention, Millicell-HA (Millipore Corporation) and standard tissue culture plastic 24 well cluster Plates (Falcon) at a density of $5 \times 10^4$ cells/cm$^2$. The Millicell HA device utilizes a tubular member to which is sealed an opaque porous membrane formed from a mixture of cellulose acetate and nitrocellulose. The seeded devices were incubated at 37°C. in an atmosphere of 7% $CO_2$, 93% air. The number of cells per device was quantitated daily for 8 days. Table 6 shows the comparative results.

TABLE 6

| Day | Plastic* (Cells/cm$^2$) | HA* (Cells/cm$^2$) | CM* (Cells/cm$^2$) |
| --- | --- | --- | --- |
| 0 | 50,000 | 50,000 | 50,000 |
| 1 | 65,000 | 42,000 | 40,000 |
| 2 | 180,000 | 130,000 | 82,000 |
| 3 | 150,000 | 250,000 | 150,000 |
| 4 | 180,000 | 460,000 | 410,000 |
| 5 | 220,000 | 490,000 | 360,000 |
| 6 | 190,000 | 450,000 | 650,000 |
| 7 | 170,000 | 520,000 | 420,000 |

TABLE 6-continued

| Day | Plastic* (Cells/cm$^2$) | HA* (Cells/cm$^2$) | CM* (Cells/cm$^2$) |
| --- | --- | --- | --- |
| 8 | 280,000 | 610,000 | 520,000 |

*Plastic = Tissue Culture Plastic
*HA = Cellulose Acetate/Nitrocellulose Membrane (0.45 micron)
*CM = Collagen Coated Poly(tetrafluoroethylene) (0.45 micron)

EXAMPLE 39

A human choriocarcinoma cell line (Be Wo, ATTC No. 98) was cultured as in Example 38 except 15% FBS was used. The membrane was coated with 100 ul of 1 part Matrigel TM which is a mixture of extracellular matrix components which promotes cell attachment, growth, and differentiation (Collaborative Research of Lexington, MA): 7 parts DMEM without FBS mixture and allowed to dry in a laminar flow hood overnight. The BeWo cells were then seeded on both the Matrigel coated membrane and standard tissue culture plastic at a density of $5 \times 10^5$ cells/cm$^2$. The cell growth on both surfaces was monitored by direct microscopic inspection and quantitated by cell counts as shown in Table 7.

TABLE 7

| Day | P* (Cells/cm$^2$) | CM* (Cells/cm$^2$) |
| --- | --- | --- |
| 0 | 500,000 | 500,000 |
| 1 | 250,000 | 123,000 |
| 2 | 400,000 | 195,000 |
| 3 | 550,000 | 730,000 |
| 4 | 516,000 | 805,000 |
| 5 | 337,000 | 1,240,000 |
| 6 | 918,000 | 1,370,000 |
| 7 | 1,240,000 | 1,490,000 |
| 8 | 1,080,000 | 1,750,000 |
| 9 | 1,400,000 | 2,220,000 |
| 10 | 1,240,000 | 1,750,000 |

P* = Tissue Culture Plastic
CM* = Matrigel Coated Poly(tetrafluoroethylene) (0.22 micron)

We claim:

1. A composite porous thermoplastic membrane which is microscopically transparent having an optical density in aqueous solution of between 0 and 0.5 when measured at 410 nanometers visible light which comprises a porous, hydrophilic polytetrafluoroethylene membrane substrate having an average pore size between 0.001 and 10 microns, said membrane substrate being directly coated on its entire surface with a cross-linked polymer having a thickness between 10 and 200 Angstroms, said cross-linked polymer formed from a monomer polymerized in situ on said substrate, in a solvent comprising a mixture of water and a water miscible organic solvent, said composite porous membrane having essentially the same porous configuration as said porous membrane substrate.

2. The composite porous membrane of claims 1 wherein said cross-linked polymer is formed from an hydroxyalkyl acrylate or methacrylate.

3. The composite porous membrane of claim 1 wherein the cross-linked polymer is formed from a hydroxyalkyl acrylate or methacrylate which is cross-linked with propylene glycol diacrylate.

4. The composite porous membrane of claim 1 wherein the cross-linked polymer is formed from a hydroxyalkyl acrylate or methacrylate which is cross-linked with tetraethylene glycol diacrylate.

5. The composite porous membrane of claim 1 wherein the cross-linked polymer is formed from an acrylamide or methacrylamide which is cross-linked with a difunctional acrylamide or methacrylamide.

6. The composite porous membrane of claim 1 wherein the cross-linked polymer is formed from a polar-substituted acrylate or methacrylate which is cross-linked with a difunctional acrylate or methacrylate.

7. The composite porous membrane of claim 1 wherein the cross-linked polymer is formed from a functionally-substituted acrylate or methacrylate which is cross-linked with a difunctional acrylate or methacrylate.

8. The composite porous membrane of claim 1, wherein the cross-linked polymer is formed from a polar substituted acrylate or methacrylate.

9. The composite porous membrane of claim 1, wherein the cross-linked polymer is formed from a multifunctional acrylate or methacrylate.

10. A device for growing cells and for viewing growth of cells which comprises a hollow tubular member having an open end and a closed end covered by the membrane of claim 1.

11. The device of claim 10 wherein said membrane is coated with a composition which promotes adhesion of cells to said membrane.

12. The device of claim 10 wherein said tubular member is transparent.

13. The device of claim 11 wherein said tubular member is transparent.

14. The device of any one of claims 10, 11, 12, or 13 wherein said second polymer is formed from a hydroxyalkyl acrylate or methacrylate.

* * * * *